Feb. 19, 1963 A. D. CARTWRIGHT, SR Plant Pat. 2,228
ILEX CORNUTA PLANT (CHINESE HOLLY)
Filed April 9, 1962
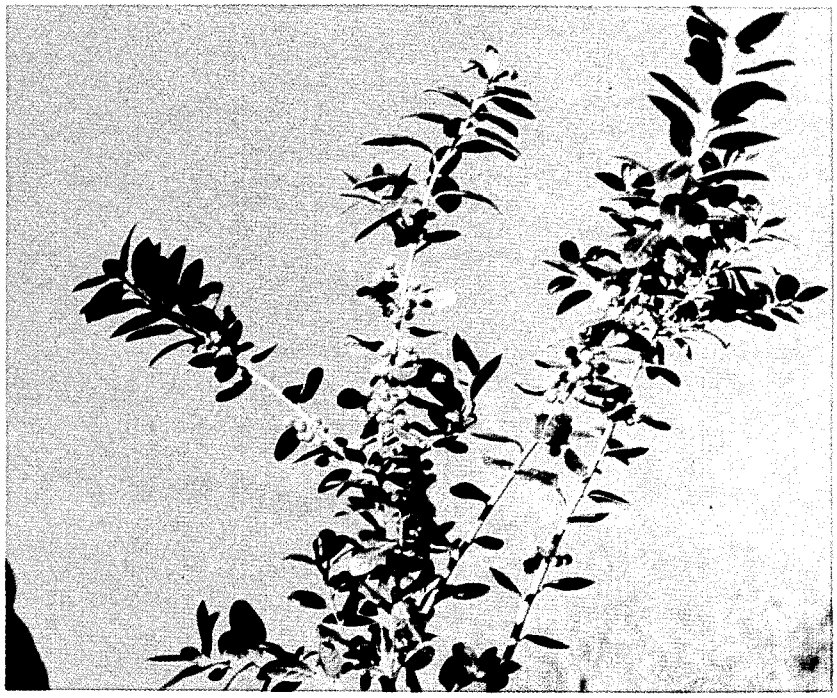
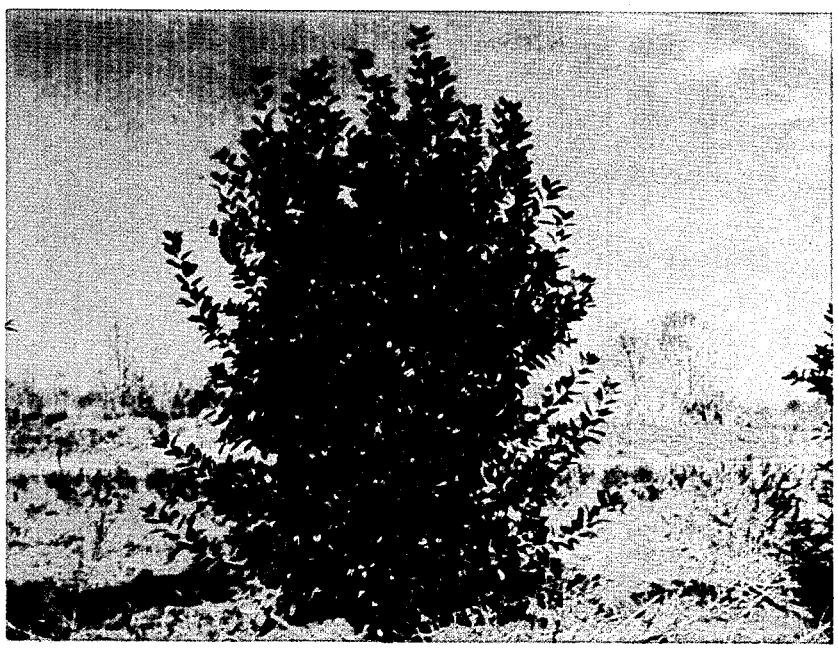
INVENTOR
ALBERT D. CARTWRIGHT, SR.
BY Lamont Johnston
ATTORNEY United States Patent Office Plant Pat. 2,228
Patented Feb. 19, 1963

2,228
ILEX CORNUTA PLANT (CHINESE HOLLY)

Albert D. Cartwright, Sr., Collierville, Tenn., assignor to Cartwright Nurseries, Collierville, Tenn., a partnership Filed Apr. 9, 1962, Ser. No. 186,285
1 Claim. (Cl. 47—59)

My invention relates to a new and improved cultivar of Chinese holly plant or *Ilex cornuta*, originating as an open pollinated or chance seedling from plants of *Ilex cornuta* in my nursery in Collierville, Tennessee.

My new cultivar was selected for its ease in propagation, transplanting, and the dark, glossy green, oblong leaves. The habit of growth is dense and compact.

Asexual propagation by cuttings of this new plant, as performed in my nursery at Collierville, Tennessee, shows that this plant reproduces true to form with the above characteristics transmitted through succeeding propagations.

References to color in the following description refer to the Horticulture Colour Chart, volumes I and II, issued by the British Colour Council and the Royal Horticultural Society. Where there are other references to color, the ordinary dictionary meanings of the terms are intended.

The accompanying illustrations show in natural color a typical branch of foliage and berries and the entire plant of this new variety.

*The Plant*

Growth habit: Dense broad (compact) upright habit of growth. Profuse ascending lateral branches. Internodes short ⅜″.

Foliage: Leaves—glabrous, oblong, 1¾″–2¼″ long, ¾″ to 1″ wide. Rounded apex with small improminent spine, base rounded, revolute entire leaf margin, alternate, coriaceous, thick, dark, glossy green.

Color: Mature upper surface, glossy, Parsley Green oo962, lower surface, Scheeles Green 860/$_1$.

Flowers: Carpellate, usually borne in fascicles, creamy white, April, produced on previous season's growth.

Fruit: Spherical 5/16″ to 7/16″ diameter; stigma—small discoid, depressed; in clusters 3 to 8. Pedicels ⅜″ to ½″ long, at base of short internodes; fruit produced readily on young plants.

Color: Blood Red 820, seed—4; 3/16″ long.

Disease and pest resistance: Highly resistant to diseases and insects, as observed under field conditions in my nursery and a comparison with other cultivars of *Ilex cornuta*.

Hardiness: Hardy without protection in zones 6*b*, 7, 8, 9, and 10, as shown in the Plant Hardiness Zone Map, Miscellaneous Publication #814, Agricultural Research Service, U.S.D.A. Additional hardiness zones to be determined in the future.

The disease and pest resistance has been demonstrated by growing this new cultivar in my nursery at Collierville, Tennessee, adjacent tother varieties of *Ilex cornuta*. While diseases are not too prevalent among *Ilex cornuta* varieties in general, this new cultivar has shown no indication of leaf spot, scale or chlorosis, while these conditions have, in some cases, been encountered in other varieties of *Ilex cornuta* grown nearby. As to hardiness, there has been no winter damage or seasonal damage to plants of this new cultivar in my nursery during the last two seasons. The same observations as to disease resistance and hardiness have been made during the last two seasons by nursery men growing this new cultivar on an experimental basis in the Memphis, St. Louis, and Philadelphia areas.

*Comparison*

This new cultivar differs from the *Ilex cornuta* cultivar "Burfordi" (unpatented) as follows:

(1) *Leaves.*—Oblong with less prominent spine and only slightly convex.

(2) *Color.*—Darker, glossy green persisting under adverse conditions.

(3) *Habit of growth.*—More compact due to shorter internodes and lateral branching habit. Small plants branch and readily develop compact and upright habit of growth.

I claim:

A new and distinct cultivar of *Ilex cornuta* (Chinese holly) plant with combination of features herein shown and described, characterized particularly by the dark, lustrous, oblong leaves and dense, upright, compact habit of growth.

No references cited.